US010624647B2

United States Patent
(12) United States Patent
Gerberding

(10) Patent No.: US 10,624,647 B2
(45) **Date of Patent: *Apr. 21, 2020**

(54) ANEURYSM DEVICES WITH ADDITIONAL ANCHORING MECHANISMS AND ASSOCIATED SYSTEMS AND METHODS

(75) Inventor: Brent Gerberding, San Jose, CA (US)

(73) Assignee: Pulsar Vascular, Inc., San Jose ( * ) Notice: Subject to any disclaimer, the term of this patent is extended or adjusted under 35 U.S.C. 154(b) by 1011 days.

This patent is subject to a terminal disclaimer.

(21) Appl. No.: 14/130,738

(22) PCT Filed: Jun. 1, 2012

(86) PCT No.: PCT/US2012/040558

§ 371 (c)(1), (2), (4) Date: Oct. 2, 2014

(87) PCT Pub. No.: WO2012/167156

PCT Pub. Date: Dec. 6, 2012

(65) Prior Publication Data

US 2015/0039015 A1 Feb. 5, 2015

Related U.S. Application Data

(60) Provisional application No. 61/493,356, filed on Jun. 3, 2011.

(51) Int. Cl.
*A61B 17/12* (2006.01)
*A61F 2/82* (2013.01)

(52) U.S. Cl.
CPC .... *A61B 17/12113* (2013.01); *A61B 17/1214* (2013.01); *A61B 17/12118* (2013.01); *A61B 17/12172* (2013.01); *A61F 2002/823* (2013.01)

(58) Field of Classification Search
CPC .......... A61B 17/12022; A61B 17/0057; A61B 2017/00588; A61B 2017/00592;
(Continued)

(56) References Cited

U.S. PATENT DOCUMENTS 3,868,956 A 3/1975 Alfidi et al.
4,164,045 A 8/1979 Bokros et al.
(Continued)

FOREIGN PATENT DOCUMENTS

AU 2006304660 A1 4/2007
CN 1384726 12/2002
(Continued)

OTHER PUBLICATIONS https://www.thefreedictionary.com/hinge, definition of the term "hinge", retrieved Aug. 18, 2019 (Year: 2019).*
(Continued)

*Primary Examiner* — David C Eastwood
(74) *Attorney, Agent, or Firm* — Troutman Sanders LLP

(57) ABSTRACT

The present technology relates to aneurysm devices with additional anchoring mechanisms, and associated systems and methods. In some embodiments, the aneurysm devices are endovascularly deliverable to a site proximate an aneurysm near a parent artery with bifurcating branches. The aneurysm devices can include a closure structure (102) comprising a distal-facing aspect configured to at least partially occlude the aneurysm and a proximal-facing aspect configured to arch over lumina of the bifurcating branches. The devices further include a supplemental stabilizer (103) connected to the closure structure. The supplemental stabilizer is configured to reside in the parent artery. The closure structure includes a hinge point (175) where the closure structure folds to form a loop element configured for anchoring within at least one of the bifurcating branches.

20 Claims, 2 Drawing Sheets

162
150
103
180a
180c
170
160
175a
175c
102
175b
175d
180b
180d
103
164
250
A
SB1
SB2
185a
185b
150
PV
240

(58) Field of Classification Search

CPC .. A61B 2017/00597; A61B 2017/0061; A61B 2017/00615; A61B 2017/00619; A61B 2017/00632; A61B 17/12027; A61B 17/12131; A61B 17/12145; A61B 17/12172; A61B 2017/00526; A61B 17/12113

See application file for complete search history.

(56) References Cited

U.S. PATENT DOCUMENTS 4,248,234 A 2/1981 Assenza et al.
4,645,495 A 2/1987 Vaillancourt
4,651,751 A 3/1987 Swendson et al.
4,665,906 A 5/1987 Jervis
4,706,671 A 11/1987 Weinrib
4,710,192 A 12/1987 Liotta et al.
4,739,768 A 4/1988 Engelson
4,820,298 A 4/1989 Leveen et al.
4,873,978 A 10/1989 Ginsburg
4,909,787 A 3/1990 Danforth
4,994,069 A 2/1991 Ritchart et al.
5,011,488 A 4/1991 Ginsburg
5,074,869 A 12/1991 Daicoff
5,122,136 A 6/1992 Guglielmi et al.
5,226,911 A 7/1993 Chee et al.
5,250,071 A 10/1993 Palermo
5,261,916 A 11/1993 Engelson
5,263,964 A 11/1993 Purdy
5,263,974 A 11/1993 Matsutani et al.
5,271,414 A 12/1993 Partika et al.
5,304,195 A 4/1994 Twyford, Jr. et al.
5,334,168 A 8/1994 Hemmer
5,342,386 A 8/1994 Trotta
5,350,397 A 9/1994 Palermo et al.
5,354,295 A 10/1994 Guglielmi et al.
5,527,338 A 6/1996 Purdy
5,531,685 A 7/1996 Hemmer et al.
5,578,074 A 11/1996 Mirigian
5,624,449 A 4/1997 Pham et al.
5,643,254 A 7/1997 Scheldrup et al.
5,665,106 A 9/1997 Hammerslag
5,669,931 A 9/1997 Kupiecki et al.
5,693,067 A 12/1997 Purdy
5,733,294 A 3/1998 Forber et al.
5,733,329 A 3/1998 Wallace et al.
5,749,890 A 5/1998 Shaknovich
5,749,894 A 5/1998 Engelson
5,759,194 A 6/1998 Hammerslag
5,766,192 A 6/1998 Zacca
5,769,884 A 6/1998 Solovay
5,797,953 A 8/1998 Tekulve
5,814,062 A 9/1998 Sepetka et al.
5,843,103 A 12/1998 Wulfman
D407,818 S 4/1999 Mariant et al.
5,895,391 A 4/1999 Farnholtz
5,895,410 A 4/1999 Forber et al.
5,910,145 A 6/1999 Fischell et al.
5,911,737 A 6/1999 Lee et al.
5,916,235 A 6/1999 Guglielmi
5,925,060 A 7/1999 Forber
5,925,062 A 7/1999 Purdy
5,925,683 A 7/1999 Park
5,928,260 A 7/1999 Chin et al.
5,933,329 A 8/1999 Tijanoc et al.
5,935,114 A 8/1999 Jang et al.
5,935,148 A 8/1999 Villar et al.
5,951,599 A 9/1999 McCrory
5,968,068 A 10/1999 Dehdashtian et al.
5,980,514 A 11/1999 Kupiecki et al.
5,980,554 A * 11/1999 Lenker ............ A61B 17/12022 606/198
5,984,944 A 11/1999 Forber
6,007,544 A 12/1999 Kim
6,013,055 A 1/2000 Bampos et al.
6,022,341 A 2/2000 Lentz
6,036,720 A 3/2000 Abrams et al.
6,063,070 A 5/2000 Eder
6,063,104 A 5/2000 Villar et al.
6,071,263 A 6/2000 Kirkman
6,077,291 A 6/2000 Das
6,081,263 A 6/2000 LeGall et al.
6,090,125 A 7/2000 Horton
6,093,199 A 7/2000 Brown et al.
6,096,021 A 8/2000 Helm et al.
6,096,034 A 8/2000 Kupiecki et al.
6,102,917 A 8/2000 Maitland et al.
6,110,191 A 8/2000 Dehdashtian et al.
6,117,157 A 9/2000 Tekulve
6,139,564 A 10/2000 Teoh
6,146,339 A 11/2000 Biagtan et al.
6,152,944 A 11/2000 Holman et al.
6,168,615 B1 1/2001 Ken et al.
6,168,622 B1 1/2001 Mazzocchi
6,174,322 B1 1/2001 Schneidt
6,183,495 B1 2/2001 Lenker et al.
6,193,708 B1 2/2001 Ken et al.
RE37,117 E 3/2001 Palermo
6,221,066 B1 4/2001 Ferrera et al.
6,221,086 B1 4/2001 Forber
6,224,610 B1 5/2001 Ferrera
6,228,052 B1 5/2001 Pohndorf
6,261,305 B1 7/2001 Marotta et al.
6,293,960 B1 9/2001 Ken
6,296,622 B1 10/2001 Kurz et al.
6,309,367 B1 10/2001 Boock
6,325,807 B1 12/2001 Que
6,344,041 B1 2/2002 Kupiecki et al.
6,344,048 B1 2/2002 Chin et al.
6,361,558 B1 3/2002 Hieshima et al.
6,375,668 B1 4/2002 Gifford et al.
6,383,174 B1 5/2002 Eder
6,398,791 B1 6/2002 Que et al.
6,478,773 B1 11/2002 Gandhi et al.
6,491,711 B1 12/2002 Durcan
6,517,515 B1 2/2003 Eidenschink
6,530,935 B2 3/2003 Wensel et al.
6,533,905 B2 3/2003 Johnson et al.
6,554,794 B1 4/2003 Mueller et al.
6,589,256 B2 7/2003 Forber
6,592,605 B2 7/2003 Lenker et al.
6,613,074 B1 9/2003 Mitelberg et al.
6,616,681 B2 9/2003 Hanson et al.
6,626,889 B1 9/2003 Simpson et al.
6,626,928 B1 9/2003 Raymond et al.
6,638,268 B2 10/2003 Niazi
6,652,556 B1 11/2003 VanTassel et al.
6,663,607 B2 12/2003 Slaikeu et al.
6,663,648 B1 12/2003 Trotta
6,669,795 B2 12/2003 Johnson et al.
6,672,338 B1 1/2004 Esashi et al.
6,679,836 B2 1/2004 Couvillon, Jr.
6,679,903 B2 1/2004 Kurz
6,689,141 B2 2/2004 Ferrera et al.
6,694,979 B2 2/2004 Deem et al.
6,723,112 B2 4/2004 Ho et al.
6,740,073 B1 5/2004 Saville
6,740,277 B2 5/2004 Howell et al.
6,746,468 B1 6/2004 Sepetka et al.
6,780,196 B2 8/2004 Chin et al.
6,790,218 B2 9/2004 Jayaraman
6,802,851 B2 10/2004 Jones et al.
6,811,560 B2 11/2004 Jones et al.
6,824,553 B1 11/2004 Samson et al.
6,835,185 B2 12/2004 Ramzipoor et al.
6,837,870 B2 1/2005 Duchamp
6,843,802 B1 1/2005 Villalobos et al.
6,855,153 B2 2/2005 Saadat
6,863,678 B2 3/2005 Lee et al.
6,890,218 B2 5/2005 Patwardhan et al.
6,911,037 B2 6/2005 Gainor et al.
6,936,055 B1 8/2005 Ken et al.
6,939,055 B2 9/2005 Durrant et al.
6,986,774 B2 1/2006 Middleman et al.

(56) References Cited

U.S. PATENT DOCUMENTS 6,994,092 B2 2/2006 van der Burg et al.
7,011,094 B2 3/2006 Rapacki et al.
7,033,374 B2 4/2006 Schaefer et al.
7,033,387 B2 4/2006 Zadno-Azizi et al.
7,122,043 B2 10/2006 Greenhalgh et al.
7,147,659 B2 12/2006 Jones
7,156,871 B2 1/2007 Jones et al.
7,169,177 B2 1/2007 Obara
7,229,461 B2 6/2007 Chin et al.
7,232,461 B2 6/2007 Ramer
7,267,679 B2 9/2007 McGuckin, Jr. et al.
7,306,622 B2 12/2007 Jones et al.
7,322,960 B2 1/2008 Yamamoto et al.
7,343,856 B2 3/2008 Blohdorn
7,387,629 B2 6/2008 Vanney et al.
7,410,482 B2 8/2008 Murphy et al.
7,569,066 B2 8/2009 Gerberding et al.
7,608,088 B2 10/2009 Jones et al.
7,662,168 B2 2/2010 McGuckin, Jr. et al.
7,857,825 B2 12/2010 Moran et al.
7,892,254 B2 2/2011 Klint et al.
8,016,853 B2 9/2011 Griffen et al.
8,075,585 B2 12/2011 Lee et al.
8,187,315 B1 5/2012 Clauson et al.
8,262,692 B2 9/2012 Rudakov
8,388,650 B2 3/2013 Gerberding et al.
8,444,667 B2 5/2013 Porter
8,470,013 B2 6/2013 Duggal et al.
8,540,763 B2 9/2013 Jones et al.
8,545,530 B2 10/2013 Eskridge et al.
8,551,132 B2 10/2013 Eskridge et al.
8,556,953 B2 10/2013 Berez et al.
8,715,312 B2 5/2014 Burke et al.
8,715,338 B2 5/2014 Frid
8,728,141 B2 5/2014 Riina et al.
8,747,430 B2 6/2014 Porter
8,771,341 B2 7/2014 Strauss et al.
8,915,950 B2 12/2014 Cam et al.
8,926,680 B2 1/2015 Ferrera et al.
8,956,399 B2 2/2015 Cam et al.
8,979,893 B2 3/2015 Gerberding et al.
9,060,886 B2 6/2015 Molaei et al.
9,107,670 B2 8/2015 Hannes et al.
9,119,625 B2 9/2015 Bachman et al.
9,179,918 B2 11/2015 Levy et al.
9,186,267 B2 11/2015 Losordo et al.
9,192,388 B2 11/2015 Cam et al.
9,211,124 B2 12/2015 Campbell et al.
9,259,229 B2* 2/2016 Abrams ........... A61B 17/12113
9,277,924 B2* 3/2016 Clarke ............ A61B 17/12022
9,636,117 B2* 5/2017 Bachman ......... A61B 17/12118
10,004,510 B2* 6/2018 Gerberding ...... A61B 17/12022
2002/0026232 A1 2/2002 Marotta et al.
2003/0033003 A1 2/2003 Harrison et al.
2003/0057156 A1 3/2003 Peterson et al.
2003/0139802 A1 7/2003 Wulfman et al.
2003/0158595 A1* 8/2003 Randall .................... A61F 2/07 623/1.13
2003/0181922 A1 9/2003 Alferness
2003/0181942 A1 9/2003 Sutton et al.
2003/0195385 A1 10/2003 DeVore
2003/0195553 A1 10/2003 Wallace et al.
2003/0212412 A1 11/2003 Dillard et al.
2004/0044391 A1 3/2004 Porter
2004/0068314 A1 4/2004 Jones et al.
2004/0087998 A1 5/2004 Lee et al.
2004/0111112 A1* 6/2004 Hoffmann ........ A61B 17/12022 606/200
2004/0158311 A1 8/2004 Berhow et al.
2004/0167597 A1 8/2004 Constantino et al.
2004/0167602 A1 8/2004 Fischell et al.
2004/0172056 A1 9/2004 Guterman et al.
2004/0193246 A1 9/2004 Ferrera
2004/0210248 A1 10/2004 Gordon et al.
2004/0210298 A1 10/2004 Rabkin et al.
2005/0021023 A1 1/2005 Guglielmi et al.
2005/0025797 A1 2/2005 Wang et al.
2005/0033409 A1 2/2005 Burke et al.
2005/0096728 A1* 5/2005 Ramer ............. A61B 17/12022 623/1.15
2005/0177224 A1 8/2005 Fogarty et al.
2006/0004436 A1 1/2006 Amarant et al.
2006/0030929 A1 2/2006 Musbach
2006/0052862 A1 3/2006 Kanamaru et al.
2006/0058837 A1 3/2006 Bose et al.
2006/0064151 A1 3/2006 Guterman et al.
2006/0106418 A1 5/2006 Seibold et al.
2006/0200234 A1 9/2006 Hines
2006/0206199 A1 9/2006 Churchwell et al.
2006/0247680 A1 11/2006 Amplatz et al.
2006/0259131 A1 11/2006 Molaei et al.
2006/0264905 A1 11/2006 Eskridge et al.
2006/0264907 A1 11/2006 Eskridge et al.
2007/0067015 A1 3/2007 Jones et al.
2007/0088387 A1* 4/2007 Eskridge .......... A61B 17/12022 606/213
2007/0106311 A1 5/2007 Wallace et al.
2007/0191884 A1 8/2007 Eskridge et al.
2007/0198075 A1 8/2007 Levy
2007/0203567 A1 8/2007 Levy
2007/0239261 A1* 10/2007 Bose ...................... A61B 17/12 623/1.15
2007/0270902 A1 11/2007 Slazas et al.
2008/0004653 A1 1/2008 Sherman et al.
2008/0004692 A1 1/2008 Henson et al.
2008/0039930 A1 2/2008 Jones et al.
2008/0103582 A1* 5/2008 Randall ..................... A61F 2/07 623/1.13
2008/0147100 A1 6/2008 Wallace
2008/0183143 A1 7/2008 Palisis et al.
2008/0221600 A1 9/2008 Dieck et al.
2008/0269774 A1 10/2008 Garcia et al.
2008/0319533 A1 12/2008 Lehe
2009/0069880 A1 3/2009 Vonderwalde et al.
2009/0125053 A1 5/2009 Ferrera et al.
2009/0299403 A1* 12/2009 Chanduszko ............. A61F 2/01 606/200
2009/0306678 A1 12/2009 Hardert et al.
2010/0023105 A1 1/2010 Levy et al.
2010/0063531 A1 3/2010 Rudakov et al.
2010/0094335 A1* 4/2010 Gerberding ...... A61B 17/12022 606/213
2011/0022149 A1 1/2011 Cox et al.
2011/0270373 A1 11/2011 Sampognaro et al.
2012/0143237 A1 6/2012 Cam et al.
2012/0143317 A1 6/2012 Cam et al.
2012/0245674 A1 9/2012 Molaei et al.
2012/0290067 A1 11/2012 Cam et al.
2012/0296361 A1 11/2012 Cam et al.
2013/0090682 A1* 4/2013 Bachman ......... A61B 17/12118 606/200
2013/0204290 A1 8/2013 Clarke et al.
2013/0268046 A1 10/2013 Gerberding et al.
2013/0268053 A1 10/2013 Molaei et al.
2013/0274862 A1 10/2013 Cox et al.
2013/0274863 A1 10/2013 Cox et al.
2013/0274866 A1 10/2013 Cox et al.
2013/0274868 A1 10/2013 Cox et al.
2013/0304109 A1* 11/2013 Abrams ........... A61B 17/12113 606/200
2014/0052233 A1 2/2014 Cox et al.
2014/0058420 A1 2/2014 Hannes et al.
2014/0121752 A1 5/2014 Losordo et al.
2014/0128901 A1 5/2014 Kang et al.
2014/0142608 A1 5/2014 Eskridge et al.
2014/0180377 A1* 6/2014 Bose ................ A61B 17/12172 623/1.11
2014/0236216 A1 8/2014 Gerberding
2015/0142025 A1 5/2015 Brandeis
2015/0142042 A1 5/2015 Cox
2015/0142043 A1 5/2015 Furey
2015/0157329 A1 6/2015 Rudakov et al.
2015/0157331 A1 6/2015 Levy et al.

(56) References Cited

U.S. PATENT DOCUMENTS

| | | | |
|---|---|---|---|
| 2015/0164512 | A1 | 6/2015 | Chin et al. |
| 2015/0164665 | A1 | 6/2015 | Cam et al. |
| 2015/0182361 | A1 | 7/2015 | Ferrera et al. |
| 2015/0196305 | A1 | 7/2015 | Meyer et al. |
| 2015/0216534 | A1 | 8/2015 | Riina et al. |
| 2015/0216687 | A1 | 8/2015 | Gerberding et al. |
| 2015/0245932 | A1 | 9/2015 | Molaei et al. |
| 2015/0250628 | A1 | 9/2015 | Monstadt et al. |
| 2015/0282962 | A1 | 10/2015 | Strauss et al. |
| 2015/0327867 | A1 | 11/2015 | Bachman et al. |
| 2015/0342612 | A1 | 12/2015 | Wu et al. |
| 2016/0015395 | A1 | 1/2016 | Molaei et al. |
| 2016/0015396 | A1 | 1/2016 | Cox et al. |
| 2016/0030050 | A1 | 2/2016 | Franano et al. |
| 2016/0038153 | A1 | 2/2016 | Losordo et al. |
| 2016/0249936 | A1 | 9/2016 | Clarke et al. |

FOREIGN PATENT DOCUMENTS

| | | | | |
|---|---|---|---|---|
| CN | 1399530 | A | 2/2003 | |
| CN | 1399531 | A | 2/2003 | |
| CN | 101489492 | A | 7/2009 | |
| CN | 102762156 | A | 10/2012 | |
| CN | 103381101 | A | 11/2013 | |
| CN | 103607964 | A | 2/2014 | |
| DE | 102008028308 | A1 | 4/2009 | |
| EP | 0820726 | A2 | 1/1998 | |
| EP | 00996372 | A1 | 5/2000 | |
| EP | 1269935 | A2 | 1/2003 | |
| EP | 1527753 | A2 | 5/2005 | |
| EP | 1951129 | A2 | 8/2008 | |
| EP | 2326259 | A1 | 6/2011 | |
| EP | 2451363 | A2 | 5/2012 | |
| EP | 2713905 | A1 | 4/2014 | |
| JP | 2001286478 | A | 10/2001 | |
| JP | 2002516705 | A | 6/2002 | |
| JP | 2003512129 | A | 4/2003 | |
| JP | 2005522266 | A | 7/2005 | |
| JP | 2009512515 | A | 3/2009 | |
| JP | 2013226419 | A | 11/2013 | |
| KR | 20080081899 | A | 9/2008 | |
| WO | WO-9724978 | A1 | 7/1997 | |
| WO | WO-9726939 | A1 | 7/1997 | |
| WO | WO-9731672 | A1 | 9/1997 | |
| WO | WO-9823227 | A1 | 6/1998 | |
| WO | WO-9850102 | A1 | 11/1998 | |
| WO | WO-9905977 | A1 | 2/1999 | |
| WO | WO-9907294 | A1 | 2/1999 | |
| WO | WO-9915225 | A1 | 4/1999 | |
| WO | WO-0013593 | A1 | 3/2000 | |
| WO | WO-0130266 | A1 | 5/2001 | |
| WO | WO-2001093782 | | 12/2001 | |
| WO | WO02/00139 | | 1/2002 | |
| WO | WO-0213899 | A1 | 2/2002 | |
| WO | WO-02071977 | | 9/2002 | |
| WO | WO-02078777 | | 10/2002 | |
| WO | WO-02087690 | | 11/2002 | |
| WO | WO-03059176 | A2 | 7/2003 | |
| WO | WO-03075793 | A1 | 9/2003 | |
| WO | WO-04019790 | A1 | 3/2004 | |
| WO | WO-04026149 | A1 | 4/2004 | |
| WO | WO-04105599 | A1 | 12/2004 | |
| WO | WO-05033409 | A1 | 4/2005 | |
| WO | WO-05082279 | A1 | 9/2005 | |
| WO | WO-2006119422 | A2 | 11/2006 | |
| WO | WO-2007/047851 | A2 | 4/2007 | |
| WO | WO-2008/151204 | A1 | 12/2008 | |
| WO | WO-2010/028314 | A1 | 3/2010 | |
| WO | WO-2011029063 | A2 | 3/2011 | |
| WO | WO 2011029063 | A2 * | 3/2011 | ....... A61B 17/12022 |
| WO | WO-2012167137 | A1 | 12/2012 | |
| WO | WO-2012167150 | A1 | 12/2012 | |
| WO | WO-2013052920 | A1 | 4/2013 | |
| WO | WO-2013169380 | A1 | 11/2013 | |
| WO | WO-2014029835 | A1 | 2/2014 | |
| WO | WO-2015179377 | A1 | 11/2015 | |

OTHER PUBLICATIONS

Cordis NeuroVascular, Inc.; “Masstransit Microcatheter,” Product Prochure; No. 153-8383-3; Miami Lakes, FL, USA (2003).

Cordis NeuroVascular, Inc.; “Prolwer Select Plus Microcatheter,” Product Brochure; No. 154-9877-1; Miami Lakes, FL, USA (2003).

Cordis NeuroVascular, Inc.; “Prowler Select LP Microcatheter,” Product Brochure; No. 155-5585; Miami Lakes, FL, USA (2004).

Cordis NeuroVascular, Inc.; “Rapid Transit Microcatheter,” Product Brochure; No. 152-7369-2; Miami Lakes, FL, USA (2003).

Extended European Search Report, European Application No. 06826291.4, dated Nov. 19, 2009, 7 pages.

Gupta et al. SMST-2003: Proc. Intl. Conf. Shape Memory Superelastic Technol.; Pacific Grove, CA; p. 639; 2003.

International Search Report and Written Opinion for International Application No. PCT/US2009/056133, dated Oct. 26, 2009, 11 pages.

International Search Report and Written Opinion for International Application No. PCT/US2010/047908, dated Mar. 15, 2012, 11 pages.

International Search Report and Written Opinion for International Application No. PCT/US2012/040552, dated Aug. 28, 2012, 14 pages.

International Search Report and Written Opinion for International Application PCT/US2012/040536, dated Oct. 15, 2012, 17 pages.

International Search Report and Written Opinion for International Application PCT/US2012/040558, dated Oct. 8, 2012, 17 pages.

International Search Report and Written Opinion for International Application PCT/US2012/059133, dated Mar. 11, 2013,15 pages.

International Search Report and Written Opinion for International Application PCT/US2013/031793, dated Jun. 26, 2013, 14 pages.

International Search Report for International Application No. PCT/US06/40907, dated May 1, 2008, 2 pages.

Micrus COPR.; “Concourse 14 Microcatheter” Product Brochure; Sunnyvale ,CA, USA.

Polytetraflouroethylene Implants, DermNet NZ, Nov. 11, 2005, http://dermetnz.org/polytetrafluoroethylene.html.

Singapore Examination Report for Singapore Application No. 200802811-0, dated Jul. 12, 2009, 7 pages.

* cited by examiner

ANEURYSM DEVICES WITH ADDITIONAL ANCHORING MECHANISMS AND ASSOCIATED SYSTEMS AND METHODS

CROSS-REFERENCE TO RELATED APPLICATION

The present application claims the benefit of U.S. Provisional Patent Application No. 61/493,356, filed on Jun. 3, 2011, and incorporated herein by reference in its entirety.

TECHNICAL FIELD

The present technology relates to implantable therapeutic devices at a target site, such as an opening at a neck of an aneurysm. In particular, the present technology is generally directed to aneurysm devices with additional anchoring mechanisms and associated systems and methods.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. The risks related to anesthesia, bleeding, and infection associated with these types of procedures are high, and tissue that is affected during the procedure may or may not survive and continue functioning.

Minimally invasive techniques for treating aneurysms are accordingly highly desirable. In general, the minimally invasive therapeutic objective is to prevent material that collects or forms in the aneurysm cavity from entering the bloodstream and to prevent blood from entering and collecting in the aneurysm. This is often accomplished by introducing various materials and devices into the aneurysm. For example, implantable vaso-occlusive metallic structures are well known and commonly used. Many conventional vaso-occlusive devices have helical coils constructed from a shape memory material or noble metal that forms a desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

It is crucial to accurately implant such vaso-occlusive devices within the internal volume of a cavity and to maintain the device within the internal volume of the aneurysm. Migration or projection of a vaso-occlusive device from the cavity may interfere with blood flow or nearby physiological structures and poses a serious health risk. In addition to the difficulties of delivering implantable occlusion devices, some types of aneurysms are challenging to treat because of structural features of the aneurysm or because of particularities of the site. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms. It is therefore challenging to position conventional implantable devices during deployment, prevent shifting or migration of such devices after deployment, and preserve blood flow in neighboring vessels following after deployment.

DETAILED DESCRIPTION

The present disclosure describes implantable therapeutic devices and methods for endovascular placement of devices at a target site, such as an opening at a neck of an aneurysm. In particular, selected embodiments of the present technology are directed to devices having additional anchoring mechanisms for lodging at bifurcated branches at the neck of the aneurysm. The following description provides many specific details for a thorough understanding of, and enabling description for, embodiments of the disclosure. Well-known structures, systems, and methods often associated with aneurysm treatment systems have not been shown or described in detail to avoid unnecessarily obscuring the description of the various embodiments of the disclosure. In addition, those of ordinary skill in the relevant art will understand that additional embodiments may be practiced without several of the details described below.

Figure 1:
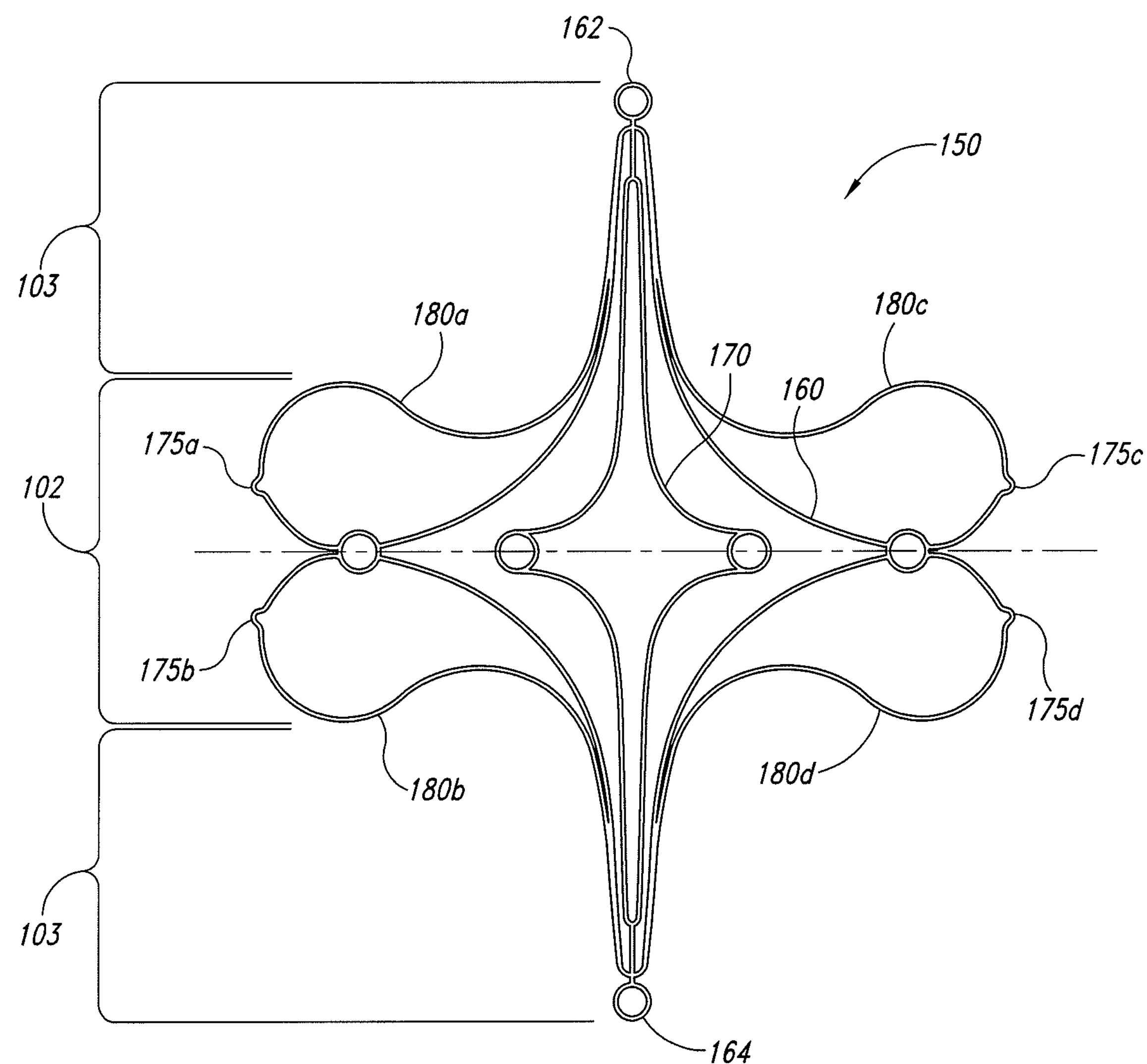
FIG. 1 is a top plan view of an aneurysm device configured in accordance with an embodiment of the technology.
Figure 2:
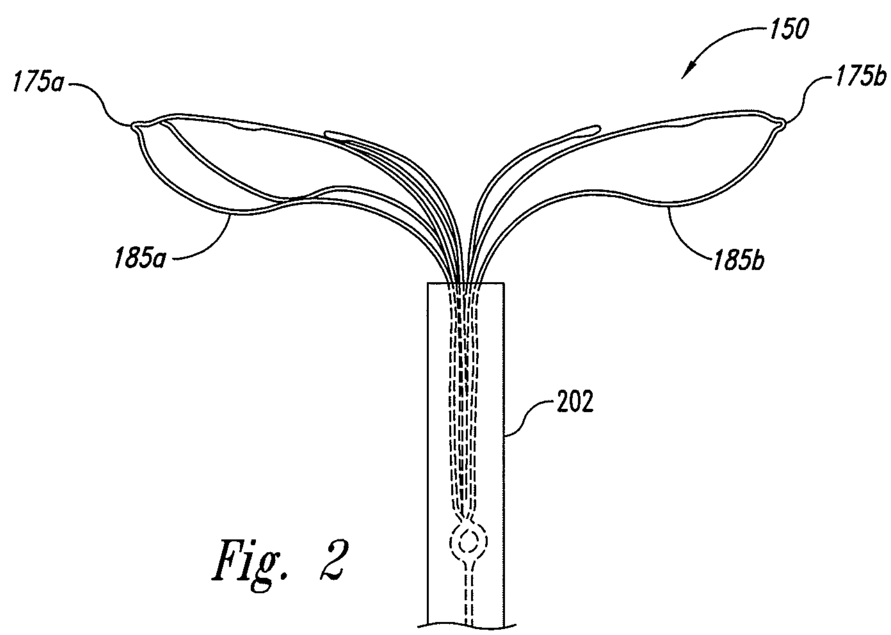
FIG. 2 is a side view of the aneurysm device of FIG. 1 in a partially deployed configuration.

FIGS. 1 and 2 illustrate an embodiment of an aneurysm device 150 configured in accordance with the present technology. In particular, FIG. 1 is a top plan view of the aneurysm device 150 in a substantially flat, pre-assembled configuration, and FIG. 2 is a side view of the aneurysm device 150 in a deployed configuration. Referring to FIG. 1, the aneurysm device 150 can comprise a closure structure 102 and a supplemental stabilizer or support 103 extending from the closure structure 102. The closure structure 102 can be a frame, scaffold, or other structure that at least partially occludes the neck of an aneurysm to prevent embolic coils or other coagulative material within the aneurysm from escaping into the bloodstream. The closure structure 102 includes a perimeter support 160 and an inner support 170. The perimeter support 160 and inner support 170 can be joined at junctions 162 and 164. The supplemental stabilizer 103 is shown in an unassembled stage in FIG. 1. Once assembled, the proximally extending sides of the closure structure 102 and the supplemental stabilizer 103 hold the curved portion of the closure structure 102 at the neck of the aneurysm.

The aneurysm device 150 can have struts 180*a-d* projecting proximally from the junctions 162 and 164. Struts 180*a* and 180*c* can be connected at junction 162 and struts 180*b* and 180*d* are connected at junction 164 to form the supplemental stabilizer 103 with proximal anchoring segments. In one embodiment, the struts 180*a-d* each include a hinge point or bend point 175*a-d*. The hinge points 175*a-d* define collapse points and allow the struts 180*a-d* to preferentially fold down in a manner that forms additional supporting elements for the aneurysm device 150 that can be lodged in side artery branches at an aneurysm neck.

In the embodiment illustrated in FIG. 1, the aneurysm device 150 is constructed from a substantially flat substrate by cutting, etching, stamping, or otherwise forming the framework of the closure structure 102, the unassembled supplemental stabilizer 103, and the hinge points 175*a-d*. The closure structure 102 and the supplemental stabilizer 103 can be constructed from a flat sheet of material having substantially uniform thickness, but in other embodiments different regions of the sheeted material can have different thicknesses corresponding to the desired thickness for portions of the closure structure 102 and/or the supplemental stabilizer 103. Further, in other embodiments the aneurysm device 150 may be formed using different techniques and/or materials.

FIG. 2 is a side view of the aneurysm device 150 in a partially deployed configuration. In particular, as the aneurysm device 150 is deployed from a delivery catheter 202, loop elements 185*a* and 185*b* form and begin to fully open. The loop elements 185*a-b* start to open as the delivery catheter 202 is being withdrawn and fully open when the delivery catheter 202 is fully withdrawn. As described in greater detail below with reference to FIG. 3, the loop elements 185*a-b* are configured to provide a mechanism for the aneurysm device 150 to anchor in bifurcated side branches when deployed across the neck of an aneurysm. In other embodiments, the loop elements 185*a-b* can have a different arrangement and/or the aneurysm device 150 may include a different number of loop elements 185.

Figure 3:
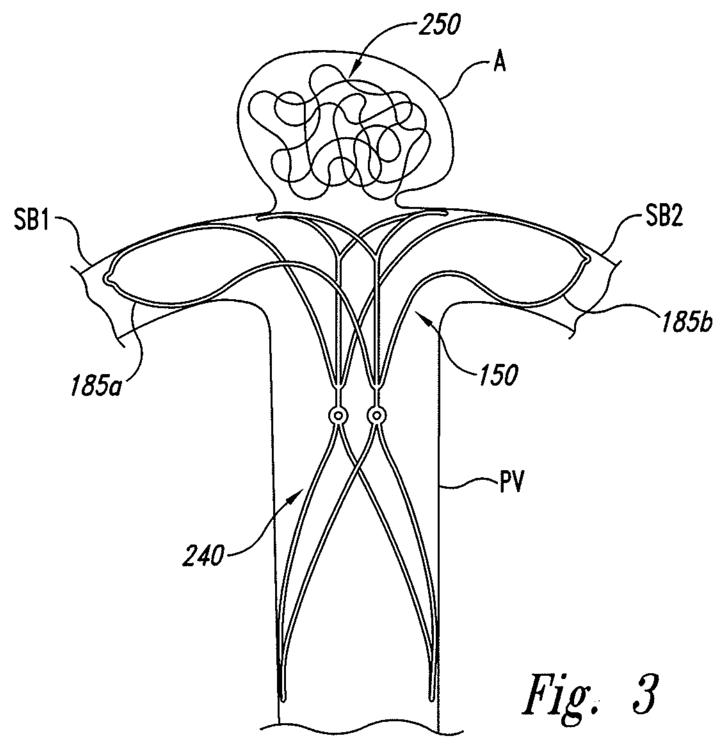
FIG. 3 is a view of the aneurysm device of FIGS. 1 and 2 deployed at the neck of an aneurysm and lodged at the bifurcated side artery branches.

FIG. 3 illustrates the aneurysm device 150 of FIGS. 1 and 2 deployed at the neck of an aneurysm A with anchoring legs 240. As mentioned above, when the aneurysm device 150 is deployed, the loop elements 185*a-b* open and can lodge in side branch vessels SB1 and SB 2, respectively. The lodging of the loop elements 185*a-b* within the side branch vessels SB 1 and SB 2 is expected to provide additional anchoring mechanisms for the aneurysm device 150 at the aneurysm A, and is expected to provide more secured lodging/deployment of the aneurysm device 150.

FIG. 3 additionally illustrates the use of the aneurysm device 150 to retain debris and/or other materials, such as an embolic coil mass 250, within the aneurysm cavity. In one embodiment, for example, implantable devices of the present technology may be deployed to retain debris and/or previously placed materials within the aneurysm cavity. In another embodiment, implantable devices of the present technology may be deployed before placing materials, such as embolic materials, coils, and the like, in the aneurismal cavity, and then the materials may be placed through the openings in the closure structure. In this situation, the aneurysm device may be retracted following placement of the embolic materials, or it may be detached and left at the site.

EXAMPLES

1. An aneurysm device endovascularly deliverable to a site proximate an artery with bifurcating branches, the aneurysm device comprising:
   - a closure structure comprising a distal-facing aspect configured to at least partially block an opening to the aneurysm and a proximal-facing aspect configured to arch over lumina of the bifurcating branches; and
   - a supplemental stabilizer connected to the closure structure, the supplemental stabilizer configured to reside in the artery;
   - wherein the closure structure includes a hinge point at which the closure structure folds to form a loop element configured for anchoring within at least one of the bifurcating branches.

2. The aneurysm device of example 1 wherein the closure structure comprises struts.

3. The aneurysm device of example 2 wherein the hinge point is formed on one of the struts.

4. The aneurysm device of example 1 wherein the closure structure comprises four hinge points.

5. The aneurysm device of example 1 wherein the closure structure is transformable between a compressed configuration and a deployed configuration.

6. The aneurysm device of example 5, further comprising a catheter configured to retain the closure structure in the compressed configuration.

7. The aneurysm device of example 1 wherein the closure structure comprises two loop elements, each individual loop element configured to lodge in one of the bifurcating branches.

8. The aneurysm device of example 1 wherein the closure structure comprises a shape memory material.

9. A system for treating an aneurysm, the system comprising:
   - a distal framework portion comprising a distal-facing aspect configured to enclose the aneurysm, wherein the distal framework includes a plurality of struts, and wherein individual struts include a hinge point; and
   - a proximal support framework connected to the distal framework portion, the support framework configured to reside in the parent artery and biased to press outward against a luminal wall thereof 10. The system of example 9, further comprising a delivery sheath configured to temporarily retain the distal framework in a compressed configuration.

11. The system of example 9 wherein the struts comprise a generally flexible material that preferentially bends at the hinge point.

12. The system of example 9 wherein the individual struts comprise a loop shape that bends at the hinge point.

13. The system of example 9 wherein the distal framework portion is formed from a generally flat, unassembled component into a three-dimensional, assembled component.

14. A method of treating an aneurysm located at a site proximate to a parent artery that bifurcates into downstream branches, the method comprising:
   - expanding an axially-compressed framework comprising a distal portion and a proximal portion at a site proximate to the aneurysm, wherein the distal portion comprises a plurality of struts having bend points; and
   - arching the distal portion of the framework unobtrusively over lumina of the downstream branches, wherein the struts comprise loops bent at the bend points, the loops configured to lodge in the downstream branches.

15. The method of example 14, further comprising forming the framework from a substantially flat material.

16. The method of example 14, further comprising delivering the framework to the site with a catheter, wherein delivering the framework comprises temporarily restraining the framework in a generally compressed configuration.

17. The method of example 14, further comprising extracting the framework from the parent artery.

18. The method of example 17 wherein extracting the framework comprises restraining the framework in a catheter in a generally compressed configuration.

19. The method of example 14, further comprising substantially enclosing the aneurysm with the distal portion of the framework.

20. The method of example 14, further comprising detaching the framework from a delivery device.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. In particular, the clot removal devices described above with reference to particular embodiments can include one or more additional features or components, or one or more of the features described above can be omitted.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, B all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An aneurysm device endovascularly deliverable to a site proximate a parent artery with bifurcating branches, the aneurysm device comprising:

a closure structure comprising a central occlusion element comprising a distal-facing aspect configured to at least partially block an opening to the aneurysm, a lodging element, and a proximal-facing aspect configured to arch over lumina of the bifurcating branches; and a supplemental stabilizer connected to the closure structure, the supplemental stabilizer configured to reside in the parent artery;

wherein the lodging element comprises struts which fold to form loop elements configured for extending into one of the bifurcating branches from the central occlusion element;

wherein each strut of the lodging element includes a hinge point offset from a centerline of the closure structure, the hinge point formed by a notch outwardly extended from a curve in the strut where the lodging element folds to form the loop elements;

wherein the notch has an apex that points generally toward an axis defined by the centerline of the closure structure.

2. The aneurysm device of claim 1 wherein the distal facing aspect comprises struts.

3. The aneurysm device of claim 2 wherein the lodging element contains a pair of hinge points disposed on opposing sides of a respective loop element.

4. The aneurysm device of claim 1 wherein the lodging element comprises two hinge points.

5. The aneurysm device of claim 1 wherein the closure structure is transformable between a compressed configuration and a deployed configuration.

6. The aneurysm device of claim 5, further comprising a catheter configured to retain the closure structure in the compressed configuration.

7. The aneurysm device of claim 1 wherein the lodging element comprises two loop elements, each loop element configured to lodge in one of the bifurcating branches.

8. The aneurysm device of claim 1 wherein the closure structure comprises a shape memory material.

9. A system for treating an aneurysm at a site proximate a parent artery with bifurcating branches, the system comprising:

a distal framework portion comprising a distal-facing aspect configured to enclose the aneurysm and lodging elements configured to extend in to the bifurcating branches in opposing directions from the distal-facing aspect, the lodging elements having a plurality of struts; and a proximal support framework connected to the distal framework portion, the support framework configured to reside in the parent artery and biased to press outward against a luminal wall thereof;

wherein each strut of the lodging elements includes a hinge point offset from a centerline of the distal framework portion where the lodging elements fold to form loop elements configured for anchoring within at least one of the bifurcating branches;

wherein the hinge point is formed by a notch outwardly extended from a curve in the strut; and wherein the notch has an apex that points generally toward an axis defined by the centerline of the distal framework portion.

10. The system of claim 9, further comprising a delivery sheath configured to temporarily retain the distal framework in a compressed configuration.

11. The system of claim 9 wherein the struts of each of the lodging elements comprise a generally flexible material, and each of the lodging elements contains a pair of hinge points disposed on opposing sides of a respective loop element.

12. The system of claim 9 wherein the struts of the lodging elements comprise a loop shape that bends at the hinge point.

13. The system of claim 9 wherein the distal framework portion is formed from a generally flat, unassembled component into a three-dimensional, assembled component.

14. A method of treating an aneurysm located at a site proximate to a parent artery that bifurcates into downstream branches, the method comprising:

expanding an axially-compressed framework comprising a distal portion and a proximal portion at a site proximate to the aneurysm, wherein the distal portion comprises a plurality of struts having bend points offset from a centerline of the distal portion; and arching the distal portion of the framework unobtrusively over lumina of the downstream branches, wherein the struts comprise loops bent at the bend points, the loops configured to lodge in the downstream branches;

wherein the bend points are formed by notches outwardly extending from curves in the struts of the distal portion;

wherein the notches have apices that point generally toward an axis defined by the centerline of the distal portion.

15. The method of claim 14, further comprising forming the framework from a substantially flat material.

16. The method of claim 14, further comprising delivering the framework to the site with a catheter, wherein delivering the framework comprises temporarily restraining the framework in a generally compressed configuration.

17. The method of claim 14, further comprising extracting the framework from the parent artery.

18. The method of claim 17 wherein extracting the framework comprises restraining the framework in a catheter in a generally compressed configuration.

19. The method of claim 14, further comprising substantially enclosing the aneurysm with the distal portion of the framework.

20. The method of claim 14, further comprising detaching the framework from a delivery device.

* * * * *